United States Patent
Polunsky et al.

[11] Patent Number: 6,042,817
[45] Date of Patent: Mar. 28, 2000

[54] POLYURETHANE FOAM LITHIUM HYPOCHLORITE COMPOSITION

[76] Inventors: Melvin S. Polunsky, 7518 N. 13th Ave., Phoenix, Ariz. 85021; George P. Heller, 2321 Normandy Dr., Irving, Tex. 75060

[21] Appl. No.: 08/988,820

[22] Filed: Dec. 11, 1997

[51] Int. Cl.[7] ............................................. A61L 9/01
[52] U.S. Cl. ........................... 424/76.1; 424/405; 424/484
[58] Field of Search .................... 424/76.1, 405, 424/484

[56] References Cited

U.S. PATENT DOCUMENTS

| | | | |
|---|---|---|---|
| Re. 29,473 | 11/1977 | Fitzgerald, Jr. .................... | 252/95 |
| Re. 31,757 | 12/1984 | Kennedy ............................ | 521/103 |
| Re. 34,065 | 9/1992 | Wainberg et al. ................. | 252/104 |
| 3,446,893 | 5/1969 | Hanford et al. ................... | 424/76 |
| 4,200,606 | 4/1980 | Kitko ................................ | 422/37 |
| 4,202,882 | 5/1980 | Schwartz .......................... | 424/76 |
| 4,249,274 | 2/1981 | Kitko ................................ | 4/227 |
| 4,281,421 | 8/1981 | Nyquist et al. ................... | 4/228 |
| 4,286,016 | 8/1981 | Dimond et al. .................. | 428/311 |
| 4,775,485 | 10/1988 | Etani ................................ | 210/696 |
| 5,016,714 | 5/1991 | McCabe et al. ................. | 166/308 |
| 5,028,408 | 7/1991 | Duncan et al. ................... | 423/497 |
| 5,075,025 | 12/1991 | Wainberg et al. ............... | 252/95 |
| 5,358,653 | 10/1994 | Gladfelter et al. ............... | 252/90 |
| 5,478,482 | 12/1995 | Jones et al. ...................... | 210/753 |
| 5,534,249 | 7/1996 | Maurer ............................. | 424/76.3 |
| 5,549,842 | 8/1996 | Chang .............................. | 510/191 |

*Primary Examiner*—S. Mark Clardy
*Assistant Examiner*—Kathryne E. Shelborne
*Attorney, Agent, or Firm*—Leander F. Aulisio

[57] ABSTRACT

A chemical composition comprising a polyester based urethane foam material impregnated or coated with an aqueous lithium hypochlorite solution, and optionally containing a quaternary ammonium compound or disodium octaborate tetrahydrate.

27 Claims, 2 Drawing Sheets

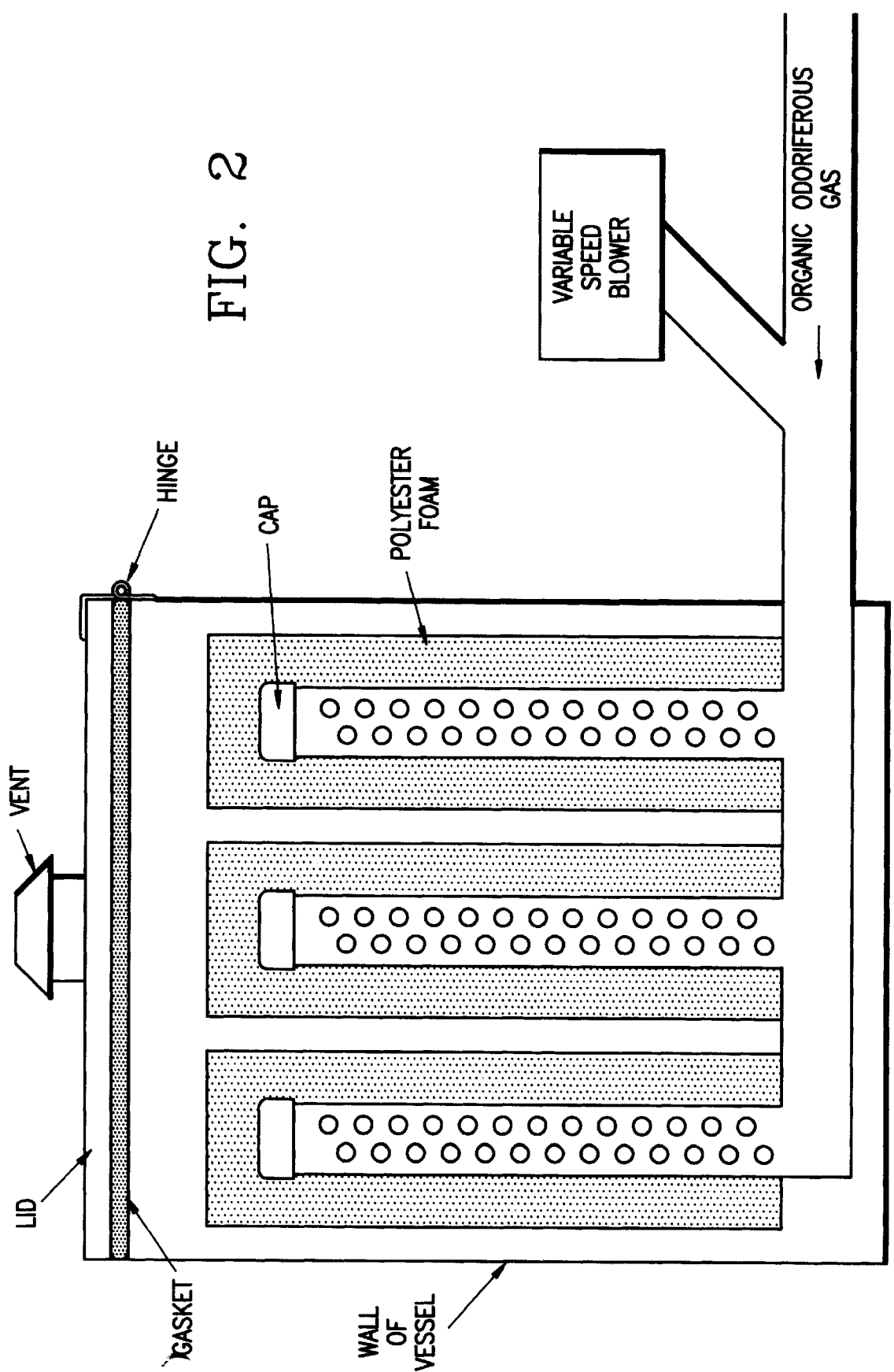

POLYURETHANE FOAM LITHIUM HYPOCHLORITE COMPOSITION

FIELD OF THE INVENTION

This invention relates to a polyurethane foam lithium hypochlorite composition useful in oxidation of odoriferous organic and inorganic chemicals.

BACKGROUND OF THE INVENTION

Odor causing materials originate from a variety of sources in the environment. Odor materials must be capable of travelling through the air to activate the olfactory senses. However the materials themselves may be solid, liquid or gaseous. Odorous materials can originate from both organic and inorganic sources; some examples of common odor causing materials in the environment are urine, feces, food waste and bilge water.

Prior art compositions for "odor control" rely heavily upon "odor-masking", rather than actually controlling or modifying the odor causing chemical. The compositions of this invention are designed to react chemically with the odor-causing agent at its source, thereby eliminating the cause of the odor rather than simply masking the effects of the odor. Typically odor masking utilizes strong, often over-bearing and even unpleasant perfumes or "masking agents". "Masking agents" are generally perfumes that simply, in a very temporary fashion, distract the olfactory sense from one unpleasant odor by means of a second, less offensive odor. When prior art compositions are used, the sense of smell is affected; with the present invention, the actual causes of odors are neutralized.

In accordance with one aspect of the present invention, there is provided a method of reducing malodor comprising the step of: delivering at or near the source of said malodor an effective amount of lithium hypochlorite to chemically neutralize the source of said malodor.

Most odor causing materials generally contain similar or common types of odor causing molecules, such as, for example, skatoles, indoles, dimethyldisulfide, amines, and ammonia. Nature eliminates odors caused by these and other chemicals by slowly combining the materials that create odors with oxygen from the air. This process is called oxidation. The compositions of the present invention achieve the same results at a greatly increased rate of speed, within minutes or even seconds.

One application for the composition of this invention is in controlling odors in portable toilets and toilets used in the transportation industry, e.g. locomotives, passenger cars, airplanes, etc. There has been interest in these compounds for use by coroners, morgues, and funeral homes. This material may also be used to eliminate human scent which could be a boon during activities such as hunting. These compositions work especially well in neutralizing odors caused by sulfurous compounds and other nitrogen containing substances such as ammonia and skatoles, as well as hydrogen sulfide. It is seen that these compositions have a wide variety of industrial applications, as well as environmentally beneficial uses.

U.S. Pat. No. 3,446,893 discloses a solid deodorizing composition comprising a solid source of available halogen, a solid gas generating source and a solid polyolefin. The solid source of available halogen is preferably lithium hypochlorite, both anhydrous and monohydrate. The solid polyolefin can be in the form of finely divided powder, spherical particles of under microns size, or fiber. The solid polyolefin is stable to available hydrogen compounds.

U.S. Pat. No. Re. 34,065 discloses a disinfectant composition which is an aqueous solution containing hypochlorite ions and a tertiary aliphatic alcohol. The composition also contains a lemon fragrance.

U.S. Pat. No. 5,075,025 discloses a disinfectant composition which is an aqueous solution containing hypochlorite ions, a tertiary aliphatic alcohol and a synthetic organic detergent. A fragrance can also be included in the composition.

U.S. Pat. No. 5,534,249 discloses a method of reducing malodor using a metal complex. The metal complex functions as an oxidation catalyst in the presence of oxygen to neutralize odor causing materials.

U.S. Pat. No. 4,202,882 discloses a method of combatting offensive odors comprising contacting the odorant with a solution containing a quaternary ammonium salt catalyst and a tetracyclic heterocycle containing four nitrogen atoms. The patent gives examples of removing odors from an environment by spraying an aqueous solution containing the quaternary compound and the heterocycle. One example refers to a truck, trailer or other cargo container in which spoiled food or seafood has left a lingering odor.

A safe, effective and easily manipulated composition is needed for contacting odoriferous materials.

SUMMARY OF THE INVENTION

The present disclosure relates to a deodorizing composition comprising a polyester based urethane foam material impregnated or coated with an aqueous solution comprising lithium hypochlorite.

The polyester based urethane foam material is in the shape of a blanket, discontinuous pieces, or a granulated, "snow" material. When discontinuous pieces or the granulated, "snow" material is employed, a pillow can be employed to enclose the pieces. The pillow must be permeable to vapors, and can be constructed from expanded polytetrafluoroethylene. In an alternative embodiment, the discontinuous pieces or "snow" material can be contained in a package which can be dissolved in water. The water soluble package can be prepared from polyvinyl alcohol or the like. Alternatively the water soluble package can contain simply an aqueous solution of lithium hypochlorite.

The present inventive disclosure further relates to a method of controlling odors arising from solid, liquid or gaseous contaminated materials comprising: locating source of odor causing material, placing polyester based urethane foam material around the source of odor causing material, optionally spraying or fogging the atmosphere in the immediate area of the odor causing material, and absorbing odors by action of the polyester based urethane foam material, wherein the polyester based urethane foam material is impregnated or coated with an aqueous solution comprising lithium hypochlorite.

The polyester based urethane foam can be easily placed around the source of odor causing material because the foam can be in the shape of a blanket, a sleeve, an insert for various containers or covers, a collection of discontinuous pieces or in the shape of a granulated, "snow" material.

BRIEF DESCRIPTION OF THE DRAWINGS

FIG. 2 is a representation of an apparatus for eliminating noxious odors in a gas stream containing a conduit for delivering odoriferous gas to a vented container, a variable speed blower, a series of foraminous pipes, and wrapped around the pipes a sleeve of polyester based urethane foam material impregnated or coated with an aqueous solution of lithium hypochlorite.

DETAILED DESCRIPTION OF THE INVENTION

Figure 1:
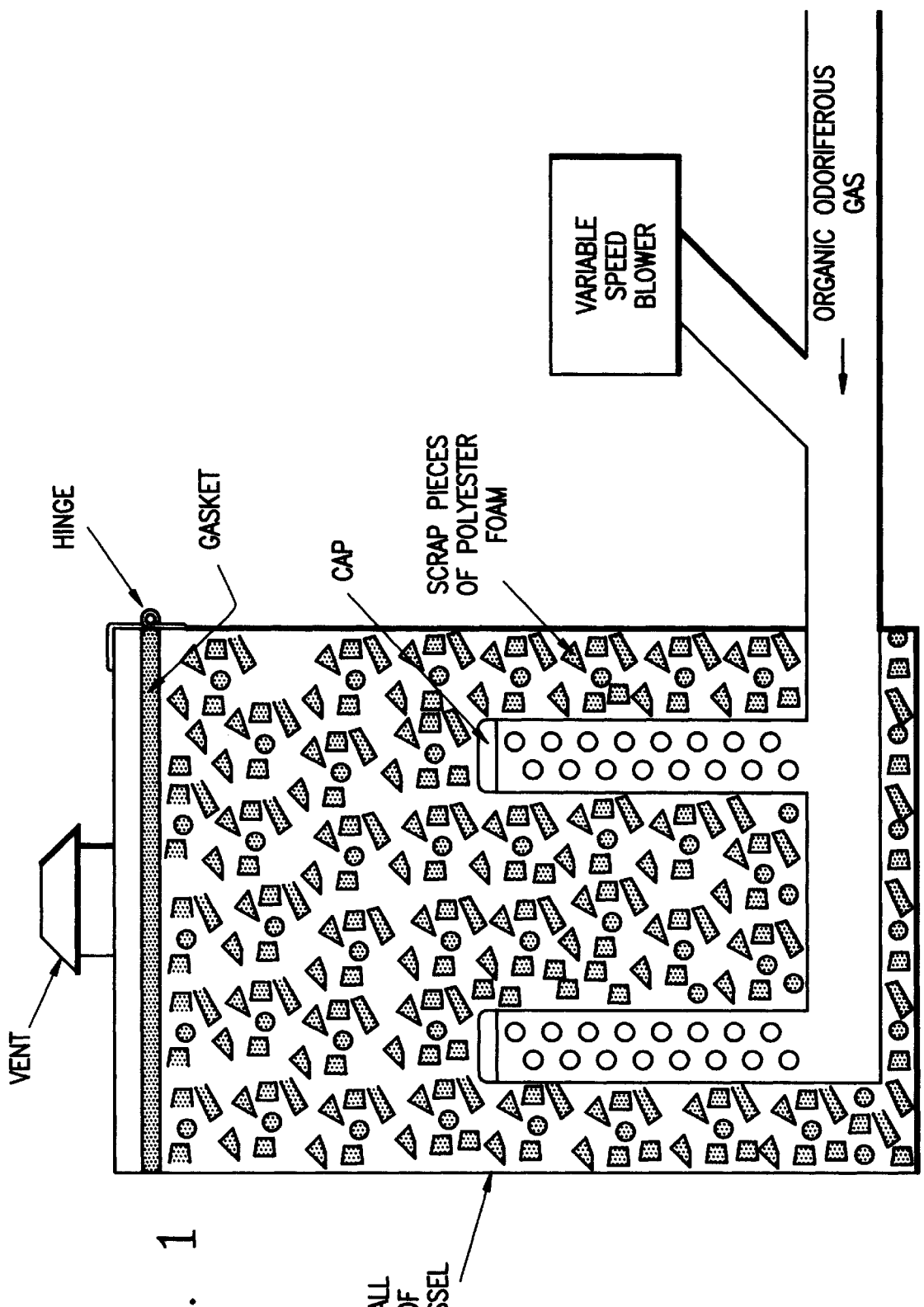
FIG. 1 is a representation of an apparatus for eliminating noxious odors in a gas stream containing a conduit for delivering odoriferous gas to a vented container, a variable speed blower, a series of foraminous pipes and scrap pieces of polyester based urethane foam material impregnated or coated with an aqueous solution of lithium hypochlorite.

Polyester based urethane foam material acts as an excellent matrix for the aqueous lithium hypochlorite solution or the aqueous mixed solution of lithium hypochlorite and disodium octaborate tetrahydrate. The polyester based urethane foam is very absorbent, has superior wicking qualities, and is relatively inert to the hypochlorite medium. The polyester based urethane foam has excellent flow through properties.

It is within the scope of the present invention to employ other absorbent material as a matrix for the aqueous lithium hypochlorite solution. Examples of other absorbent materials are polyether based urethane foam material, activated carbon, molecular sieves, natural and synthetic zeolite materials, clay materials, cellulosic materials, xanthan gums and other naturally occurring or synthetic gums, ceramic materials, silica, titania, peanut shells, corn cobs, burlap straw and the like.

The polyester based urethane foam material is preferably a polymer prepared from a polyol, a polycarboxylic acid and a diisocyanate. A diamine is usually employed as a catalyst. Examples of the foam which can be employed in the present composition and method are polyester based urethane foams distributed by INOLEX Chemical Company, Philadelphia, Pa. 19148.

The lithium hypochlorite is present in the aqueous solution in an amount of about 0.01% to about 5% by weight. In a preferred embodiment, the lithium hypochlorite is present in the aqueous solution in an amount of about 0.3% by weight to about 5% by weight. Most preferably, the lithium hypochlorite is present in an amount of about 3% by weight.

In an alternative embodiment, the aqueous solution further comprises disodium octaborate tetrahydrate. In a preferred embodiment, the disodium octaborate tetrahydrate is present in the aqueous solution in an amount of about 0.01% to about 3% by weight.

In a second alternative embodiment, the lithium hypochlorite aqueous solution further comprises a quaternary ammonium compound. The quaternary ammonium compound is present in the aqueous solution in an amount of about 0.005% to about 0.1% by weight. Alternatively, an aqueous solution of a quaternary ammonium compound can be a separate part of a dual treatment system comprising a first aqueous solution of lithium hypochlorite and a second aqueous solution of a quaternary ammonium compound. Such a system is especially useful in treatment of pit potties.

Various quaternary ammonium salts are known to have a slight deodorizing ability and are even used commercially for this purpose. The primary function of these salts is that of a germicide killing the bacterial responsible for the decomposition of organic matter thereby generating odors. These salts are generally prepared by causing the reaction of a benzyl or alkyl halide, sulfonate, or sulfate with a ternary base (e.g. a tertiary amine). The usual salts are the halides, such as chloride and bromide, sulfates, methosulfates, ethosulfates and benzenesulfonates.

Among the preferred quaternary ammonium salts for the compositions of the invention are those having the formula

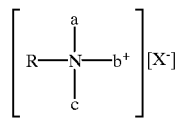

wherein R is an aliphatic radical of 8 to 20 carbon atoms, X is an anion such as halide, sulfate, nitrate, carbonate, phosphate, lower alkyl sulfate, lower alkanesulfonate, saccharinate, sulfamate, benzenesulfonate, lower alkylbenzenesulfonates with 1 to 10 alkyl carbon atoms, etc., and a, b and c may differ and are selected from the group consisting of lower alkyl, phenyl lower alkyl, phenoxy lower alkyl, thienyl, lower alkenyl, lower alkynyl, substituted phenyl lower alkyl, and a and b could form a heterocyclic ring with c being an aliphatic radical of 1 to 20 carbon atoms. These and other suitable quaternary ammonium salts are described in Schwartz et al., Surface Active Agents and Detergents, Vol. II, (1958), pp. 112–118. The term "lower" is intended to mean 1 to 7 carbon atoms.

Examples of specific quaternary ammonium salts are BTC 2125 M (equal parts of n-alkyl dimethyl benzyl ammonium chlorides where the n-alkyl is 14 to 18 carbon atoms and n-alkyl dimethyl ethyl benzyl ammonium chlorides where n-alkyl is 12 to 14 carbon atoms), BTC 1100 (n-dodecyl dimethyl 1-naphthylmethyl ammonium chloride monohydrate), BTC 471 (alkyl dimethyl benzyl ammonium chloride), Hyamine 1622 (diisobutyl phenoxy ethoxyethyl dimethyl benzyl ammonium chloride), Hyamine 2389 (80% of methyl dodecyl benzyl trimethyl ammonium chloride and 20% of methyl dodecyl xylene bis-trimethyl ammonium chloride), Barquat MS100 (alkyl dimethyl benzyl ammonium chloride dihydrate), etc. Although most commercial quaternary ammonium salts are the chlorides, other salts are just as suitable for the present invention.

The aqueous solution containing hypochlorite ions may optionally have present therein one or more additional ingredients. Thus, for example, the aqueous solution may also contain a synthetic organic detergent, such as sodium dodecyl sulphate. Thus, for example, for each part by weight of compound providing hypochlorite ions, there may be present from about 0.005 to about 0.1 part by weight, preferably about 0.02 part by weight, of synthetic organic detergent, such as sodium dodecyl sulphate.

The aqueous solution containing hypochlorite ions may also optionally have present therein one or more chlorine-stable fragrances. Suitable fragrances for use herein include virtually any fragrance that is stable to hypochlorite, e.g., benzaldehyde, lavender oil, lemon oil, methyl salicylate, phenylethyl alcohol, and the like. Such fragrances will generally be present in an amount such that for each part by weight of hypochlorite compound there is present from about 0.005 to about 0.2 part by weight of fragrance, most preferably about 0.02 part by weight of fragrance, most preferably a lemon fragrance.

The amount of fragrance may vary according to the strength and volume of the fragrance used. A weaker fragrance may be present to an extent of 0.2% w/w whereas a stronger fragrance may be present to an extent of 0.02% w/w. The synthetic organic detergent, such as sodium dodecyl sulphate, not only provides a cleaning power to the disinfectant but it also helps to dissolve or maintain the fragrance in solution. Since suitable fragrances mentioned above are usually oil-based fragrances, the synthetic organic detergent may be used to dissolve the fragrance prior to addition to the aqueous solution and thereafter it maintains the fragrance in solution. When a fragrance is present to an extent of from about 0.005 to about 0.2% w/w, the range of detergent may generally be from about 0.005 to about 0.01% w/w. Quantities of detergent in excess of this amount may be present to provide additional detergency to the solution.

Other optional ingredients may be present in the aqueous solution such as a chlorine stable coloring agent.

The aqueous solutions of this invention are useful in destroying pathogens including viruses, bacteria and fungi.

The aircraft environment is very special in its requirements for safety. Aircraft toilets are self-containing units possessing holding tanks, recirculating pumping systems and a special antifreeze fluid to both cleanse the interior of the system and prevent any odor formation that could permeate the air in the cabin of the aircraft. Odor control in this unit has historically been accomplished by utilizing high concentrations of formaldehyde to kill bacteria and denature proteins. This approach has been relatively effective. However, as is well-known, formaldehyde is a gas. Even at standard pressure, at sea level, the vapor pressure of this gas is sufficient to release the gas from aqueous solution. At cruising altitudes, aircraft cabin pressure is considerably reduced below that of 760 millimeters of mercury. In this lower-pressure atmosphere, formaldehyde gas escapes from the aqueous fluid used in the aircraft toilet system at an increased rate. Entering the aircraft's ventilation system, formaldehyde gas becomes recirculated throughout the aircraft interior. On long, transcontinental or transoceanic flights, the concentration of formaldehyde in the atmosphere can reach levels sufficient to cause eye and respiratory irritation. This necessitates the rapid exchange of contaminated air for fresh, outside air. This is a costly proposition in terms of fuel. Also, in recent years, it has become increasingly well-known that formaldehyde is a potential carcinogenic agent. For this reason, its use has come into disfavor. Replacements for the odor control characteristics of formaldehyde are needed, not only in the aircraft environment, but also in other semi-closed/isolated environments. These include boats, campers, buses, and trains, among others. Thus, a composition for use in eliminating odors associated with self-contained toilet must be safe, must have a low toxicity and must be non-corrosive to equipment. As mentioned above, this is especially important in the case of aircraft utility.

Carpeting, both domestic and commercial, is often subject to heavy traffic and abuse. In eating establishments, for example, both patrons and employees use and abuse carpeting by spilling foodstuffs which become embedded in the fibers of the carpeting. It has been found that these materials oftentimes find their way into the carpet padding and even into the flooring material under the carpeting. General cleaning of spillage areas has been found lacking in its ability to remove residual odors generated by fatty materials and proteinaceous compounds are decomposed by bacterial and inherent chemical activities such as the tendency of butterfat, for instance, to hydrolyze with the release of the highly odoriferous butyric acid. It is impossible to effectively eliminate such odors by simply using masking agents, as found in the prior art. Strong chemical reagents such as oxidizing compounds found in bleaches destroy the integrity of the carpeting. Their use destroys the flooring as well as the odor. Foul odors in restaurants or in home carpeting are highly objectionable from an aesthetic standpoint and require safe, nondestructive and efficient elimination.

A desirable product to remove carpet odors would be one which can be applied to the surface of a carpet and which would penetrate through the carpeting to the odor source, where chemical reaction would eliminate the odor source. The product may not have any odor of its own, so as not to be detectable by persons in the immediate vicinity of use. The product should be colorless, if possible, so as not to "stain" or otherwise discolor the carpeting. It must be non-toxic so as not to contaminate the environment with potentially dangerous chemical substances.

Building remediation involves special problems, including removal of pet odors, sewage odors, odor from burned out buildings and the like. It has been observed that use of aqueous solutions of lithium hypochlorite can be employed to successfully reduce and eliminate odors during building remediation. After treatment with lithium hypochlorite, buildings should be contacted with sodium thiosulfate in a post treatment or post fogging operation in order to reduce and eliminate harmful effects to human and animal inhabitants.

The polyester based urethane foam material can be shaped into various forms for different applications. The impregnated foam material can be inserted into a vent stack. It can be constructed in the shape of a sleeve to fit over a perforated vent. The material can be fabricated to fit over a vessel emitting odoriferous gas, e.g. a grease trap or vessel, a rendering truck, a casket, a garbage dumpster. The material can be manufactured in the shape of an insert for a manhole cover, or in the shape of a vent for a body bag.

The treated polyester based urethane foam material can be employed as an air filtration membrane in various air pollution control systems such as portable air cleaning systems, sick room deodorizers, fire restoration deodorizers, electrostatic air filters, HVAC systems and the like.

The impregnated polyester based urethane foam material of the present disclosure can be employed in a variety of air pollution control systems. Pit potties, doctors' offices, coroners' rooms, animal shelters, analytical laboratories, synthetic chemical laboratories, grease traps, body bags, caskets, rendering trucks, garbage cans, fields treated with organic fertilizers, bathrooms and building renovations are all areas which can benefit from employing the present disclosure. Other environmental areas which will benefit from application of the present disclosure are chemical scrubbers, sewage systems, locker rooms, sump pumps, shower stalls, public telephone stalls, restaurants, food stores and the like.

The use of lithium hypochlorite in rejuvenation of dry chemical scrubber containing carbon is also disclosed. The carbon can be either removed and then treated with an aqueous lithium hypochlorite solution, or contacted in situ with the hypochlorite solution.

The polyester based urethane foam material impregnated with an aqueous solution of lithium hypochlorite is useful in destroying pathogens including viruses, bacteria and fungi in any number of environmental areas including hospitals, restaurants, home cleaning and the like.

It is sometimes desirable to spray an odoriferous area with an aqueous solution of lithium hypochlorite. The solution contains about 0.01% to 5% by weight lithium hypochlorite. In a preferred embodiment, the solution contains 0.1% to 4% by weight lithium hypochlorite. Most preferably, the solution contains 1% by weight lithium hypochlorite.

The lithium hypochlorite solution can be delivered to the odoriferous area as a mist or fog by employing an aerosol generator system such as a DYNA-FOG® electric ULV cold aerosol spray mist applicator. Dispersal flow rates and particle sizes can be adapted to the specific environment.

In a preferred embodiment, the aqueous lithium hypochlorite solution is delivered as a mist or fog by an aerosol generator system in combination with the use of the polyester based urethane foam material impregnated with an aqueous lithium hypochlorite solution. As an example, an impregnated polyester based urethane foam blanket can be placed over dead animals and the area can be "fogged" with a mist of aqueous lithium hypochlorite solution. The result is that odoriferous chemicals are oxidized and removed from the air.

Any number of techniques may be employed to prepare the inventive composition, as within the knowledge of one skilled in the art.

The following examples serve to further illustrate the nature of the invention and are not intended to implicitly or expressly restrict the nature thereof.

EXAMPLE 1

A roll of polyester based urethane foam obtained from Hickory Springs Company is cut into blanket-size pieces. The pieces are individually dipped into a vat containing an aqueous solution of 3% by weight lithium hypochlorite in deionized water. Each piece is submerged in the vat for a time of about 2 minutes and ambient temperature.

After contact with the aqueous lithium hypochlorite solution, each blanket piece is withdrawn from the vat and air dried at room temperature for a time of about 1 hr to 4 hrs to obtain a final product of polyester based urethane foam blanket impregnated with lithium hypochlorite. The product is found to be stable for an extended period of time.

EXAMPLE 2

A roll of polyester based urethane foam obtained from Hickory Springs Company is cut into small pieces. the pieces are charged into a vat containing an aqueous solution of 3% by weight lithium hypochlorite in deionized water. The pieces are submerged in the vat for a time of about 2 minutes at ambient temperature.

After contact with the aqueous lithium hypochlorite solution, the pieces are withdrawn from the vat and air dried at room temperature for a time of about 1 hr to 4 hrs to obtain a final product of polyester based urethane foam pieces impregnated with lithium hypochlorite. The product is found to be stable for an extended period of time.

EXAMPLE 3

A structure of interengaged pieces of IMPAC™ from Lantec Products, Inc. is removed to a vat containing an aqueous solution of 3% by weight lithium hypochlorite in deionized water. The interengaged pieces are made from polypropylene. The structure is submerged in the vat for a time of about 10 minutes at ambient temperature.

After contact with the aqueous lithium hypochlorite solution, the structure is withdrawn from the vat and air dried at room temperature for a time of about 1 hr to 4 hrs to obtain a final product of a structure of interengaged pieces impregnated with lithium hypochlorite. The product is found to be stable for an extended period of time.

EXAMPLE 4

A roll of polyester based urethane foam obtained from Hickory Springs Company is cut into blanket-size pieces. The pieces are individually charged into a vat containing an aqueous solution of 3% by weight lithium hypochlorite and 0.5% by weight disodium octaborate tetrahydrate in deionized water. Each piece is submerged in the vat for a time of about 2 minutes at ambient temperature.

After contact with the aqueous solution of lithium hypochlorite and disodium octaborate tetrahydrate, each blanket piece is withdrawn from the vat and air dried at room temperature for a time of about 1 hr to 4 hrs to obtain a final product of polyester based urethane foam blanket impregnated with lithium hypochlorite and disodium octaborate tetrahydrate. The product is found to be stable for an extended period of time.

EXAMPLE 5

About 5 lbs. of polyester based urethane foam material in the form of "snow" (granulated) is obtained. The "snow" material is placed in a porous retaining vessel and charged to a vat containing an aqueous solution of 3% by weight lithium hypochlorite in deionized water. The material is submerged into the vat for a time of about 2 minutes and at ambient temperature.

After contact with the aqueous lithium hypochlorite solution, the material is withdrawn from the vat and air dried at room temperature for a time of about 1 hr to 4 hrs to obtain a final product of polyester foam "snow" material impregnated with lithium hypochlorite. The product is found to be stable for an extended period of time.

We claim:

1. A deodorizing composition comprising a polyester based urethane foam material impregnated or coated with an aqueous solution comprising unencapsulated lithium hypochlorite.

2. The composition according to claim 1 wherein the polyester based urethane foam material is in the shape of a blanket.

3. The composition according to claim 1 wherein the polyester based urethane foam material is in the shape of discontinuous pieces.

4. The composition according to claim 1 wherein the lithium hypochlorite is present in the aqueous solution in an amount of about 0.1% to about 5.0% by weight.

5. The composition according to claim 1 wherein the aqueous solution further comprises disodium octaborate tetrahydrate.

6. The composition according to claim 5 wherein the disodium octaborate tetrahydrate is present in the aqueous solution in an amount of about 0.01% to about 3.0% by weight.

7. The composition according to claim 1 wherein the aqueous solution further comprises a quaternary ammonium compound.

8. The composition according to claim 7 wherein the quaternary ammonium compound is present in the aqueous solution in an amount of about 0.005% to about 0.1% by weight.

9. The composition according to claim 4 wherein the lithium hypochlorite is present in an amount of about 3% by weight.

10. A method of controlling odors arising from solid, liquid or gaseous contaminated materials comprising the steps of:

locating source of odor causing material;

placing polyester based urethane foam material around the the source of odor causing material;

optionally spraying or fogging the atmosphere with an aqueous solution of lithium hypochlorite in the immediate area of the odor causing material; and absorbing odors by action of the polyester based urethane foam material, wherein the polyester based urethane foam material is impregnated or coated with an aqueous solution comprising lithium hypochlorite.

11. The method according to claim 10 wherein the polyester based urethane foam material is in the shape of a blanket.

12. The method according to claim 10 wherein the polyester based urethane foam material is in the shape of discontinuous pieces.

13. The method according to claim 10 wherein the lithium hypochlorite is present in the aqueous solution in an amount of about 0.1% to about 5.0% by weight.

14. The method according to claim 13 wherein the lithium hypochlorite is present in an amount of about 3% by weight.

15. The method according to claim 10 wherein the aqueous solution further comprises disodium octaborate tetrahydrate.

16. The method according to claim 15 wherein the disodium octaborate tetrahydrate is present in the aqueous solution in an amount of about 0.01% to about 3.0% by weight.

17. The method according to claim 10 wherein the aqueous solution further comprises a quaternary ammonium compound.

18. The method according to claim 17 wherein the quaternary ammonium compound is present in the aqueous solution in an amount of about 0.005% to about 0.1% by weight.

19. The composition according to claim 1 wherein the polyester based urethane material comprises a polymer prepared from a polyol, a polycarboxylic acid and a diisocyanate.

20. The method according to claim 10 wherein the polyester based urethane material comprises a polymer prepared from a polyol, a polycarboxylic acid and a diisocyanate.

21. A method of controlling odor arising from a pit pottie comprising the step of:

placing an aqueous solution comprising lithium hypochlorite into the pit pottie.

22. The method according to claim 21 wherein the lithium hypochlorite is present in the aqueous solution in an amount of about 0.1% to about 5.0% by weight.

23. The method according to claim 22 wherein the lithium hypochlorite is present in the aqueous solution in an amount of about 3% by weight.

24. A method according to claim 21 further comprising the step of placing an aqueous solution comprising a quaternary ammonium compound into the pit pottie.

25. A method of rejuventating a dry chemical scrubber containing carbon comprising the steps of:

placing polyester based urethane foam material into contact with the carbon;

optionally contacting the carbon in situ with an aqueous solution of lithium hypochlorite; and absorbing odors by action of the polyester based urethane foam material, wherein the polyester based urethane foam material is impregnated with an aqueous solution comprising lithium hypochlorite.

26. The composition according to claim 1 wherein the polyester based urethane foam is in the shape of granulated, "snow" material.

27. The method according to claim 10 wherein the polyester based urethane foam material is in the shape of a granulated, "snow" material.

* * * * *